United States Patent [19]

Sinnett et al.

[11] Patent Number: 4,670,006

[45] Date of Patent: Jun. 2, 1987

[54] FLUID AND AIR INFUSION DEVICE

[76] Inventors: Kevin B. Sinnett, 102 Kilps Court West, Waukesha, Wis. 53186; Rodger L. White, 434 Lyman, Oconomowoc, Wis. 53066

[21] Appl. No.: 907,143

[22] Filed: Sep. 12, 1986

Related U.S. Application Data

[63] Continuation of Ser. No. 661,361, Oct. 16, 1984, abandoned.

[51] Int. Cl.$^4$ .............................................. A61M 1/00
[52] U.S. Cl. ........................................ 604/26; 604/35; 604/67; 604/119
[58] Field of Search ............... 128/DIG. 12, DIG. 13; 623/3; 604/22, 26, 65, 67, 118, 121, 50, 245; 73/708

[56] References Cited

U.S. PATENT DOCUMENTS

| | | | |
|---|---|---|---|
| 3,572,319 | 3/1971 | Bittner et al. | 604/118 |
| 3,812,855 | 5/1974 | Banko | 604/31 |
| 3,885,590 | 5/1975 | Ford et al. | 604/26 |
| 3,902,495 | 9/1975 | Weiss et al. | 604/22 |
| 3,982,534 | 9/1976 | Buckman | 604/246 |
| 4,082,893 | 4/1978 | Okita | 3/1.7 |
| 4,084,612 | 4/1978 | Baehr | 604/118 |
| 4,094,318 | 6/1978 | Burke et al. | 128/DIG. 13 |
| 4,117,843 | 10/1978 | Banko | 604/65 |
| 4,136,700 | 1/1979 | Broadwin et al. | 604/22 |
| 4,202,218 | 5/1980 | Romo | 73/708 |
| 4,206,437 | 6/1980 | Wu | 73/708 |
| 4,207,887 | 6/1980 | Hiltebrandt et al. | 604/26 |
| 4,261,360 | 4/1981 | Perez | 128/DIG. 13 |
| 4,306,552 | 11/1981 | Cannon | 604/65 |
| 4,395,258 | 7/1983 | Wang et al. | 604/67 |
| 4,451,251 | 5/1984 | Osterholm | 604/26 |

OTHER PUBLICATIONS

"Textbook of Medical Physiology" by A. Guyton, M.D.; W. B. Saunders Co., 1971.

*Primary Examiner*—Lee S. Cohen
*Assistant Examiner*—David Shay
*Attorney, Agent, or Firm*—Glenn A. Busé

[57] ABSTRACT

The fluid infusion device includes a primary and an auxiliary fluid pump capable of providing a substantially continuous flow of a fluid, such as air. A pressure regulator driven by a reversible electric motor regulates the air pressure and the flow of pressurized air through an disposable air delivery unit, consisting of a millipore, bacterial static filter and a tube removably connected to an air outlet is controlled by a normally closed, solenoid-operated infusion valve. Separate pressure transducers detect the pump output pressure, the regulator outlet or preset pressure, and the infusion pressure downstream of the infusion valve when it is open. An electrical control system includes indicating circuits for providing visual readouts of the preset and infusion pressures, a motor control circuit for selectively changing the level of electrical power supplied to the regulator motor so that the presure setting of the regulator can be changed at a "slow" speed or a "rapid" speed, and underpressure detections circuit for initiating operation of the auxiliary pump in the event the pump outlet pressure decreases below a predetermined level and an overpressure detection circuit for closing the infusion valve and triggering an alarm circuit in the event the infusion pressure increases above a predetermined level. Operation of the regulator and the infusion valve can be controlled by push button switches on a front panel or remotely by a foot switch assembly connected to the electrical circuit.

13 Claims, 6 Drawing Figures

FLUID AND AIR INFUSION DEVICE

This application is a continuation of Ser. No. 661,361 filed Oct. 16, 1984, now abandoned.

This invention relates to fluid infusion devices. In one aspect, this invention relates to fluid infusion devices capable of delivering fluid at accurately controlled pressures for use in various medical applications and the like, such as vitrectomy surgery.

In vitrectomy surgery, the vitreous gel is removed from the eye and a fluid, such as air, is infused into the vitreous cavity at a pressure of approximately about 22-23 mm Hg to prevent the eye from collapsing. Mechanical syringes have been used for this purpose. Vitrectomy surgery takes a considerable period of time. Consequently, as the surgery is being performed, multiple injections from relatively large syringes is required to keep the vitreous cavity filled with air. After a syringe is emptied, the eye can collapse during the time the syringe is being refilled, creating a potential damaging situation.

Pumping devices have been used to deliver a continuous flow of air at a pressure up to about 50 mm Hg. However, the commercially available pumping devices known to applicants include one or more of the following shortcomings. The actual pressure being delivered can be several mm Hg different (usually less) than that indicated by the device. The operator must manipulate a manual knob or the like on a front panel to adjust the pressure being delivered and, consequently, the pressure cannot be both rapidly and slowly adjusted up and down in an accurately controlled manner. All other control buttons, switches, and the like are also located on the device itself and must be operated by hand. There is no adequate means for insuring adequate delivery of air in the event there is a larger than normal leakage from the vitreous cavity, internal leakage in the device, or pump failure.

An object of the invention is to provide a fluid infusion device which is capable of accurately indicating the actual pressure of the fluid being delivered.

Another object of the invention is to provide a fluid infusion device which can be operated by a remote control mechanism, such as a foot-operated switch assembly.

A further object of the invention is to provide a fluid infusion device including a control for both rapidly and slowly adjusting the pressure of the fluid being delivered.

A still further object of the invention is to provide a fluid infusion device adapted for use in vitrectomy surgery and including means for automatically maintaining the pressure of the fluid delivered to vitreous cavity at a predetermined pressure in the event there is excessive leakage from the vitreous cavity, internal leakage in the device, or pump failure.

A yet further object of the invention is to provide a fluid infusion device including means for preventing delivery of the fluid at a pressure above a predetermined level.

Other objects, aspects, and advantages of the invention will become apparent to those skilled in the art upon reviewing the following detailed description, the drawings and the appended claims.

SUMMARY OF THE INVENTION

The invention provides a fluid infusion device including a fluid pump for delivering a substantially continuous flow of a fluid, such as air, an adjustable pressure regulator connected in fluid communication with the pump outlet for varying the pressure of fluid delivered from a pressurized fluid outlet, an electrically-operated infusion valve connected in fluid communication with the regulator outlet and movable between open and closed positions to control the fluid flow from the regulator to the fluid outlet, separate electrical pressure detectors for detecting the pressure in the conduit between the regulator outlet and the infusion valve and a conduit between the infusion valve and the fluid outlet and producing electrical signals representative of a preset pressure and an infusion pressure, respectively, indicating means for receiving these signals and providing visual readouts of the preset and infusion pressures, and a reversible electric motor operably connected to the regulator adjustment means for adjusting the regulator in opposite directions to increase and decrease the pressure of the fluid delivered through the fluid outlet. The pump, motor, infusion valve, and pressure detecting means are electrically interconnected in an electrical control system including indicating circuits for receiving the signals from the pressure detectors and producing readouts of the preset pressure and the infusion pressure and a motor control for selectively driving the motor in opposite directions to increase and decrease the preset pressure. The indicating circuits preferably include temperature compensation means so that the visual readouts of the preset and infusion pressures are substantially the same as the actual pressures when the temperature inside the device is within the range of about 60° to 120° F.

When the device is used for vitrectomy surgery, a disposable fluid delivery unit including a millipore, bacterial static filter and a length of tubing can be removably connected to the pressurized fluid outlet. The inside diameter of the tubing and the pore size of the filter preferably is large enought to prevent a substantial pressure drop in the fluid flowing therethrough and yet the pore size of the filter is small enough for it to remain bacterial static.

In one embodiment, the motor control circuit is arranged so that the level of electrical power supplied to the gear motor can be selectively changed to drive the motor at a "slow" speed and at a "rapid" speed and thereby selectively change the speed at which the preset pressure is adjusted.

In one embodiment, a foot switch assembly is provided for remotely controlling operation of the regulator gear motor and the infusion valve.

In one embodiment, an auxiliary pump is connected in fluid communication with the primary pump and the electrical system includes an underpressure detecting circuit for initiating operation of the auxiliary pump when the pump outlet pressure decreases below a predetermined value because of a failure with the primary pump, a larger than normal leakage from the vitreous cavity during surgery, or internal leakage in the device.

In one embodiment, the electrical system includes an overpressure detection circuit for producing an overpressure signal in the event the pressure being delivered through the fluid outlet exceeds a predetermined level. The overpressure signal causes the infusion valve to be closed and can be used to trigger an alarm circuit which activates an audible alarm.

DESCRIPTION OF THE PREFERRED EMBODIMENTS

The fluid infusion device of the invention can be adapted for a variety of applications where the introduction of a substantially continuous flow of a gas or liquid at a relatively low pressure and under precisely controlled conditions is required. It is particularly adaptable for infusing air into the evacuated vitreous cavity of a human eye during vitrectomy surgery and will be described in connection with that application.

Figure 1:
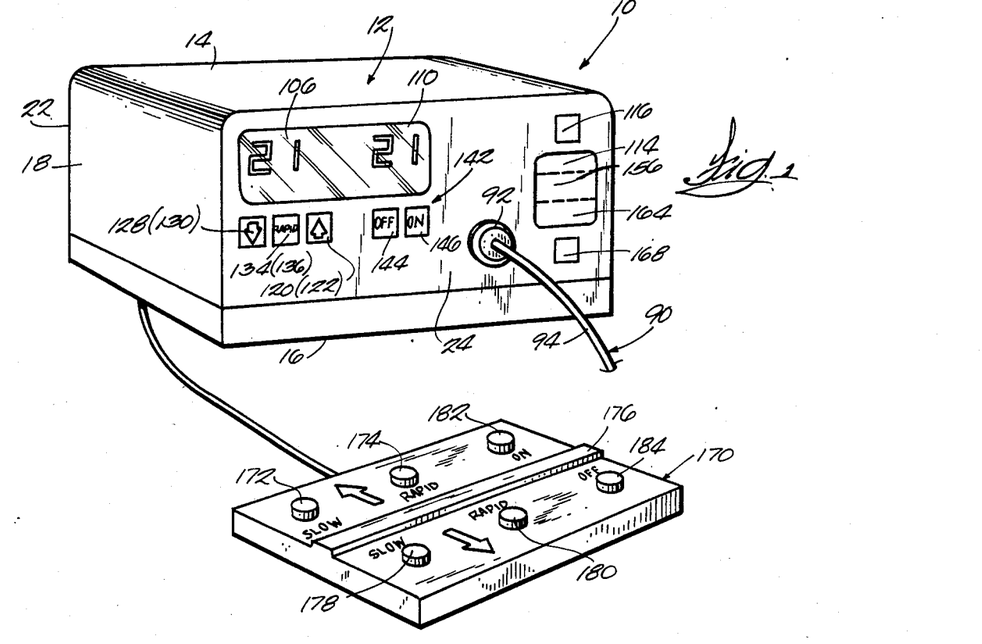
FIG. 1 is a perspective view of a fluid infusion device embodying the invention.
Figure 2:
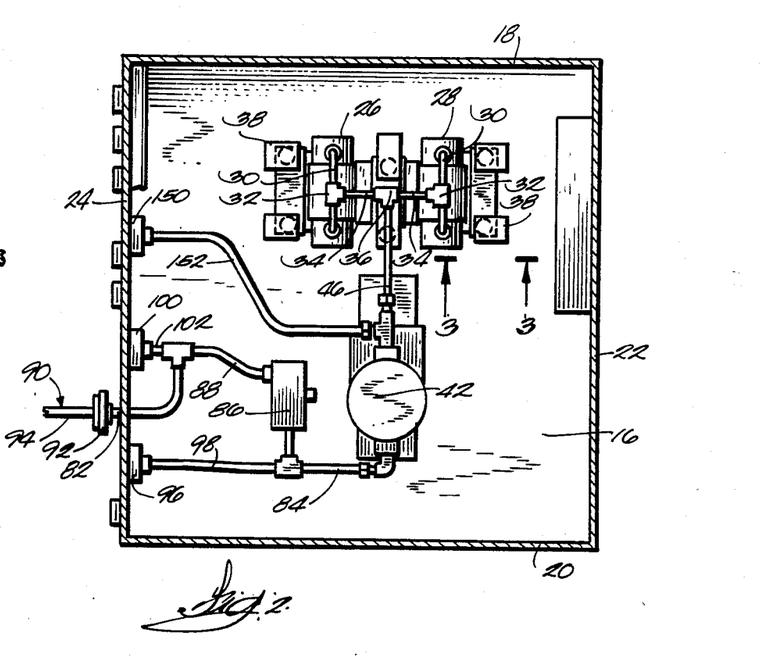
FIG. 2 is a partially schematic, top view of the fluid infusion device illustrated in FIG. 1, shown with the top of the housing removed.
Figure 3:
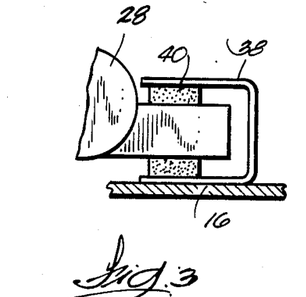
FIG. 3 is an enlarged sectional view taken generally along line 3—3 in FIG. 2.

Referring to FIGS. 1-3, the air infusion device 10 includes a housing 12 having opposed top and bottom walls 14 and 16, opposed side walls 18 and 20, a back wall 22 and a front wall or panel 24. Mounted on the bottom wall 16 inside the housing 12 is a primary air pump 26 and an auxiliary air pump 28.

The pumps 26 and 28 are a conventional type capable of providing a substantially continuous flow of air at relatively low pressures. In the specific embodiment illustrated, each pump has a pair of diaphragms (not shown) which simultaneously move in opposite directions (i.e., alternately move toward and away from each other). The outlet or pressure chambers for the diaphragms in each pump are connected to a conduit 30 including a T-fitting 32 to provide a single pump outlet 34. The outlets 34 of the primary and auxiliary pumps 26 and 28 are connected to a T-fitting 36.

The primary and auxiliary pumps 26 and 28 preferably are shock mounted to minimize noise and vibration. In the specific embodiment illustrated, the pumps are mounted on the housing bottom wall 16 by a mounting fixture 38 including elastomeric mounts 40 as best shown in FIG. 3. As described in more detail below, the primary pump 26 operates when electrical power to the device is turned on and the auxiliary pump 28 is automatically turned on in the event of an underpressure condition.

The output pressure from the primary pump and/or the auxiliary pump 28 is regulated by a pressure regulator 42 including an inlet port 44 connected in fluid communication with the T-fitting 36 via a conduit 46. The pressure regulator 42 can be any conventional type capable of providing a controlled flow of air at a pressure from 0 up to about 50 mm Hg. In the specific embodiment illustrated, the pressure regulator 42 (FIG. 4) is a diaphragm type including a body 48 having a flexible diaphragm 56 dividing the interior of the body 48 into a pressure chamber 52 and a spring chamber 54 which is vented to the atmosphere through a vent port 56. Pressurized air from the primary pump 26 and/or the auxiliary pump 28 enters the pressure chamber 52 through an opening 58 connected in fluid communication with the inlet port and exits from the pressure chamber 52 through an outlet port 60. The flow of air into the pressure chamber 52 is metered by a valve member 62 which seats over the opening 58 for opening and closing and is carried on a lever arm 64 fulcrumed at 66. The lever arm 64 is connected to the diaphragm 50 and the valve member 62 opens and closes the opening 58 in response to upward and downward movement of the diaphragm 50, respectively.

Figure 4:
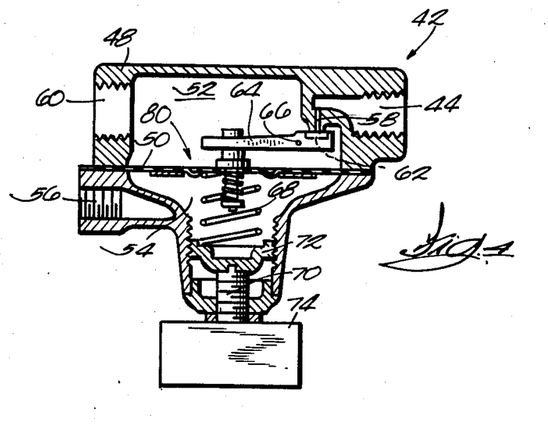
FIG. 4 is an enlarged cross sectional view of the pressure regulator.

Disposed in the spring chamber 54 is a spring 68 which bears against the diaphragm 50 and urges it upwardly. The spring 68 keeps the valve member 62 in the open position until the force acting on the top side of the diaphragm 50 exceeds the combined spring force and pressure force acting on the underside of the diaphram 50.

The regulated pressure exiting from the outlet port 60 is set by turning a shaft 70 which is threaded into the regulator body 48 and is connected to and rotates with a spring retainer 72 also threaded into the regulator body 48. Operably connected to the shaft 70 is reversible, electrical gear motor 74 (illustrated diagramatically in FIGS. 3 and 5) which can be selectively operated by a motor control circuit described in more detail below to either rapidly or slowly rotate the shaft 70 in opposite directions to inrease or decrease the pressure setting. The upper and lower pressure settings are governed by limit switches 76 and 78 (illustated diagramatically in FIG. 6) operably connected to the shaft 70 in a suitable manner.

In the specific embodiment illustrated, a conventionally arranged relief valve assembly 80, carried by the diaphragm 50, opens when the pressure in the pressure chamber 52 exceeds a predetermined level governed by adjustment of the shaft 70 and allows excess pressure to bleed to the atmosphere through the vent port 56.

Since the diaphragm 50 is located above the spring 68, its weight and the weight of the relief valve assembly 80 and a portion of the lever arm 64 produces a gravitational force tending to move the valve member 62 to the closed position, thereby assuring that the regulator 42 can be adjusted to substantially absolute zero.

Pressurized air is delivered from the pressure regulator 42 to an air outlet 82 on the front of the panel 24 via a conduit 84, an electrically operated air infusion valve 86 and a conduit 88. Pressurized air is delivered from the air outlet 82 to the site of surgery by a disposable fluid delivery unit 90 including a 0.22 millipore, bacterial static filter 92 and a length of sterile flexible tubing 94. The inside diameter of the tubing 94 and the pore size of the filter 92 is large enough to prevent a substantial pressure drop in the air flowing therethough at a pressure up to about 50 mm Hg and a flow rate which exists under normal conditions during vitrectomy surgery. Such an arrangement permits the pressure of the air being delivered to the surgery site to be substantially the same as that being delivered through the air outlet 82.

The fluid delivery unit is removed and discarded after each use. The air infusion valve 86 preferably is a normally-closed, solenoid-operated valve. The pressure regulator 42 initially is preset when the air infusion valve 86 is in the normally closed position. The pressure present in the conduit 84 downstream of the pressure regulator 42 (preset pressure) is detected by an electrical pressure transducer 96 mounted on the back side of the front panel 24 and connected in fluid communication with the conduit 84 via a conduit 98. The preset pressure transducer 96 produces an electrical signal representative of the preset pressure.

The pressure of the air in the conduit 88 downstream of the air infusion valve 86 (infusion pressure) is detected by an electrical pressure transducer 100 mounted on the backside of the front panel 24 and connected in fluid communication with the conduit 88 and the air outlet 82 via a conduit 102. The infusion pressure transducer 100 produces an electrical signal representative of the infusion pressure or the pressure being delivered through the tube 94 of the fluid delivery unit 90.

Figure 5:
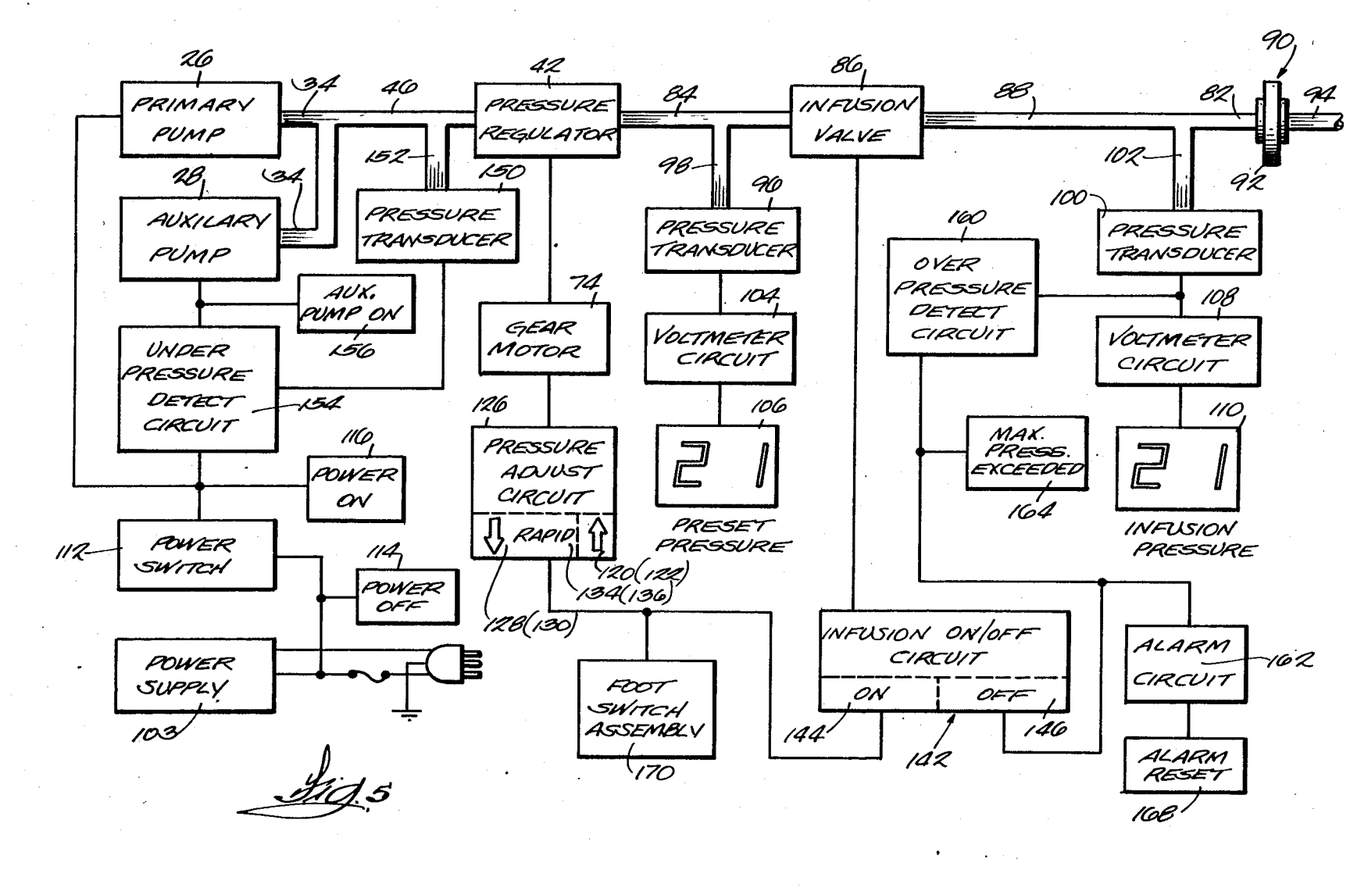
FIG. 5 is a simplified block diagram of various mechanical and electrical components of the fluid infusion device illustrated in FIG. 1.
Figure 6:
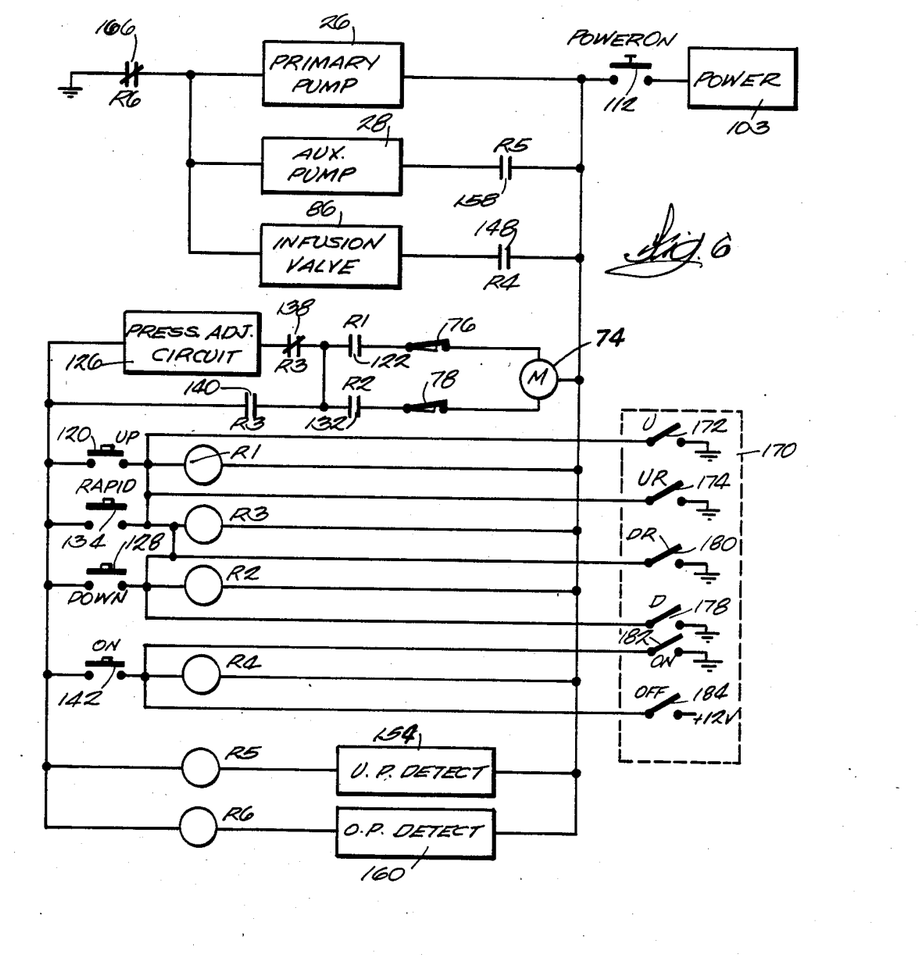
FIG. 6 is a simplified diagramatic representation of a portion of the electrical control circuit.

The air infusion device 10 includes an electrical control system, portions of which are illustrated by block diagram in FIG. 5 and schematically in FIG. 6. The electrical system interconnects the primary pump 26, the gear motor 74, the air infusion valve 86, the preset pressure transducer 96 and the infusion pressure transducer 100 to a suitable 12-volt power supply 103. The electrical system includes indicating means for receiving the signals from the preset pressure transducer 96 and the infusion pressure transducer 100 and producing visual readouts of these two pressures.

In the specific embodiment illustrated, the electrical system includes a voltmeter circuit 104 connected to the preset pressure transducer 96 and a light emitting diode 106 mounted on the front panel 24 for providing a digital readout of the preset pressure in mm Hg. The electrical system also includes a voltmeter circuit 108 connected to the infusion pressure transducer 100 and a light emitting diode 110 mounted on the front panel 24 for providing a digital readout of the infusion pressure in mm Hg. The voltmeter circuits 104 and 108 are of generally conventional design, preferably in the form of a chip, except that each includes a temperature compensating circuit which can accommodate temperatures inside the housing when the range of about 60° to about 120° F. and still provide a readout within plus or minus 1 mm Hg of the pressure actually existing in the conduits 84 and 88.

The electric system includes a push-push type, on/off power switch 112 mounted on the front panel 24. A "power off" light 114 on the front panel 24 is illuminated when the power switch 112 is the off position. When surgery is being performed in a dimly lit or dark room, the "power off" light 114 provides sufficient illumination to see the push button for the power switch 112. A "power on" light 116 on the front of the panel 24 is illuminated and the primary pump 26 is started when the power switch 112 is depressed to the on position. At the same time, the preset pressure and the infusion pressure light emitting diodes 106 and 110 are energized. Diode 106 shows the pressure setting of the pressure regulator 42.

An "up" light 122 (upwardly pointing arrow in FIGS. 1 and 5), a "down" light 130 (downwardly pointing arrow in FIGS. 1 and 5), a "rapid" light 136, an infusion "off" light 144, and an infusion "on" light 146 on the front of the panel 24 all are illuminated when the power switch 112 is depressed to the on position so that the push buttons for the respective switches described below are visible in a dimly lit or dark operating room.

The electrical system includes a motor control circuit for selectively driving the gear motor 74 in opposite directions to increase and decrease the pressure setting of the pressure regulator 42. This motor control circuit preferably also includes means for selectively changing the level of electrical power supplied to the gear motor 74 so it can be operated at "slow" speed or at a "rapid" speed and thereby change the speed at which the pressure setting of the regulator is increased or decreased.

In the specific embodiment illustrated, the motor control circuit (FIG. 6) includes a momentary push button switch 112 (up) on the front panel which, upon being depressed, and energizes a relay R1 to close its normally open contacts 122 and supply electrical power to the gear motor 74 through a pressure adjustment circuit 126 to drive the gear motor 74 at a "slow" speed in the direction for increasing the pressure setting of the pressure regulator 42. The pressure adjustment circuit 126 can be a conventional pulse modulating type circuit which produces a periodic pulse output to drive the gear motor 74 at a speed less than when a full voltage is continuously supplied.

The motor control circuit includes a second momentary push button switch 128 (down) on the front panel 24 which, upon being depressed, energizes a relay R2 to close its normally open contacts 132 and supply electrical power to the gear motor 74 through the pressure adjustment circuit 126 to drive the gear motor at a "slow" speed in the direction for increasing the pressure setting of the pressure regulator 42. When the gear motor is operated at the "slow" speed, the preset pressure can be changed in accurate increments of 1 mm Hg.

The motor control circuit includes a third momentary push button switch 134 (rapid) on the front panel 24 which, upon being depressed, energizes a relay R3 to open its normally closed contacts 138 and close its normally open contacts 140. Simultaneous depression of either the up switch 120 or the down switch 128 causes electrical power to be supplied directly to the gear motor 74 (i.e., by passes the pressure adjustment circuit 126) and drives the gear motor 74 at a "rapid" speed in one direction or the other, depending upon whether the up switch or the down switch is depressed.

The electrical system includes an infusion switch 142 on the front panel 24 including on and off buttons. The infusion valve 86 is in its normally closed position when the infusion switch 142 is in the off position. Depression of the on button of the infusion switch 142 energizes a relay R4 to close its normally open contacts 148 and electrical power is supplied to the solenoid of the infusion valve 86 to energize it to the open position. The infusion valve 86 is closed by depressing the off button of the infusion switch 126.

The infusion valve 86 preferably is a three-way valve and is arranged so that the entire system downstream of the infusion valve, including the fluid delivery unit, is vented to the atmosphere when the infusion valve is in the closed position.

The device preferably includes means for automatically turning on the auxiliary pump 28 in the event the pressure being delivered through the fluid delivery unit 90 is less than a predetermined level because of a failure of the primary pump 26, a larger than normal leakage from the vitreous cavity during surgery, or internal leakage in the device. In the specific embodiment illustrated, the pump outlet pressure is detected by an electrical pressure transducer 150 (underpressure) mounted on the backside of the front panel 24 and connected in fluid communication with the conduit 46, upstream of the pressure regulator 42, via a conduit 152. The underpressure transducer 150 produces an electrical signal representative of the pump output pressure.

The electrical system includes an underpressure detecting circuit 154 connected to the underpressure transducer 150. In the event, the pressure detected by the underpressure transducer 150 decreases below a predetermined level (e.g., 60 mm Hg), an output signal from the underpressure detection circuit 154 causes illumination of an "auxiliary pump on" light 156 and energizes a relay R5 to close its normally open contacts 158 and electrical power is supplied to operate the auxiliary pump 28.

The device preferably is provided with an overpressure protection system which automatically closes the infusion valve, sounds an audible alarm, and vents the system in the event the pressure of the air being delivered through the fluid delivery unit 90 exceeds a predetermined level. In the specific embodiment illustrated, the electrical system includes an overpressure detection circuit 160 electrically connected to the infusion pressure transducer 100 and an alarm circuit 162. In the event the pressure detected by the infusion pressure transducer 100 increases above a predetermined level (e.g., 40 mm Hg), an output signal from the overpressure detection circuit 160 causes illumination of a "maximum pressure exceeded" light 164, triggers the alarm circuit 162 which energizes an audible alarm (not shown) and energizes a relay R6 to open its normally closed contacts 166 and terminate electrical power to the infusion valve 86 and the primary pump 26 and/or the auxiliary pump 28. The infusion valve 86 closes and the entire system downstream thereof is immediately vented to atmosphere. Once the pressure detected by the transducer 100 decreases below the predetermined level, the alarm circuit can be reset by depressing an alarm reset button 168 on the front panel 124.

The device preferably includes a foot switch assembly 170 which can be used to selectively adjust the pressure regulator at both "slow" and "rapid" speeds and to selectively open and close the infusion valve 86. As illustrated in FIG. 1, the foot switch assembly 170 includes a relatively flat, box-like unit 171 housing four push button switches for adjusting the pressure regulator, a "slow" up switch 172 and a "rapid" up switch 174 on one side of a lateral extending rib 176 and a "slow" down switch 178 and a "rapid" down switch 180 on the other side of the rib 176. The unit 171 also houses two push button switches for opening and closing the infusion valve, an infusion valve "on" switch 182 on one side of the rib 174 and infusion valve "off" switch 184 on the other side of the rib 176.

As shown in FIG. 6, the foot switch assembly 170 is connected to the electrical circuit so that depression of the "slow" up switch 172 and the "slow" down switch 178 energizes relays R1 and R2, respectively, and the gear motor 74 is operated as described above. Depression of the up "rapid" switch 174 energizes both relay R1 and relay R3 and depression of the down "rapid" switch energizes both relay R2 and relay R3 and the gear motor 74 operates as described above. Depression of the infusion valve "on" switch 182 energizes relay R4 and the infusion valve 86 is opened as described above. Depression of infusion valve "off" switch 184 deenergizes relay R4 because both poles of the relay are connected to the power supply.

It should be understood that FIG. 6 is a simplified schematic representation of the actual electrical circuitry and is intended to illustrate the functional relationship of various components. Consequently, it illustrates apparently inoperable circuit connections. For instance, in actual practice, the lead from the up "rapid" switch 174 on the foot switch assembly is not connected to both relays R1 and R3 in the manner illustrated and the lead from the down "rapid" switch 180 is not connected to both relays R2 and R3 in the manner illustrated.

After the device has been plugged into a 115 volt AC outlet, operation is commenced by pressing the power switch 116 which starts the primary pump 26. The desired infusion pressure is set by simultaneously depressing both the up switch 120 and the rapid switch 134 on the front panel 24 or stepping on the "rapid" up switch 172 on the foot switch assembly 170. The present pressure is displayed in mm Hg by the light emitting diode 106. As the desired preset pressure is approached, final adjustment can be made by depressing only the up switch 130 on the front panel 24 or stepping on the "slow" up switch 172 on the foot switch assembly 170.

After the fluid delivery unit 90 is installed on the air outlet 82, air flow can be started by depressing the infusion on switch 146 on the front panel 24 or stepping on the on switch 182 on the foot assembly 170. The pressure being delivered to the fluid delivery unit 90 is displayed in mm Hg by the light emitting diode 110.

If the pressure in the vitreous cavity drops during surgery because of multiple incisions or the like, the surgeon can conveniently raise the preset pressure to compensate for this by stepping on either the "slow" up switch 172 or the "rapid" up switch 174 on the foot switch assembly 170 until the infusion pressure reaches the desired level. If the need arises, a surgeon can decrease the infusion pressure by stepping on either the "slow" down switch 178 or the "rapid" down switch 180 on the foot switch assembly 170. Flow of air can be terminated by stepping on the off switch 184 on the foot switch assembly 170 and started again by stepping on the on switch 182.

In the event the infusion pressure drops below the predetermined level because of excess leakage from the virtreous cavity, the primary pump fails, etc., the auxiliary pump is automatically turned on as described above, thereby minimizing potential collapsing of the eye. In the event the infusion pressure exceeds a predetermined level which could be damaging to the eye, the infusion valve is automatically closed and an audible alarm sounds as described above, thereby minimizing potential injury to the eye.

From the above description, it can be seen that the fluid infusion device provided by the invention, while having a simple construction, is capable of providing continuous flow of a fluid at an accurately controlled pressure and an accurate visual readout of the actual pressure of the infusion fluid being delivered to the surgery site. Also, the device includes means for preventing undesirable overpressure and underpressure conditions and a conveniently operated control for either incrementally or rapidly adjusting the infusion pressure before the start of and during infusion and for initiating and terminating infusion.

We claim:
1. A fluid infusion device comprising a housing;
a fluid outlet in said housing;
an electrically-operated fluid pump for delivering a substantially continuous flow of a fluid disposed in said housing and having an outlet;

a pressure regulator disposed in said housing and having an outlet, an inlet connected in fluid communication with said pump outlet via first conduit means and movable adjustment means for varying the pressure of the fluid delivered from said regulator outlet;

an electrically-operated infusion valve disposed in said housing and having an inlet connected in fluid communication with said regulator outlet via second conduit means and an outlet connected in fluid communication with said fluid outlet via third conduit means, said infusion valve being movable between an open position to permit fluid flow from said regulator to said fluid outlet and a closed position to prevent fluid flow from said regulator to said fluid outlet;

first pressure detecting means for detecting the fluid pressure in said second conduit means and producing a signal representative of a preset pressure;

second pressure detecting means for detecting the fluid pressure in said third conduit means and producing a signal representative of an infusion pressure substantially corresponding to the pressure of the fluid delivered through said fluid outlet;

a reversible electric motor operably connected to said regulator adjustment means for moving said adjustment means in opposite directions to increase and decrease the pressure of the fluid delivered from said regulator outlet; and an electrical system electrically interconnecting said pump, said motor, said infusion valve, and said pressure detecting means; said electrical system including, first indicating means for receiving said preset pressure signal and providing a visual read out of the preset pressure, second indication means for receiving said infusion pressure signal and providing a visual read out of the infusion pressure, and a motor control circuit for selectively driving said motor in opposite directions to increase and decrease the preset pressure and including pressure adjustment means for selectively changing the level of electrical power supplied to said motor to selectively drive said motor at a "slow" speed and at a "rapid" speed and thereby selectively change the speed at which the preset pressure is adjusted.

2. A fluid infusion device according to claim 1 including a disposable fluid delivery unit removably connected to said fluid outlet and including a tube and a millipore, bacterial static filter, the inside diameter of said tube and the pore size of said filter being large enough to prevent a substantial pressure drop in the fluid flowing therethrough and yet the pore size of said filter being small enough to remain bacterial static.

3. A fluid infusion device according to claim 1 wherein said pressure adjustment means includes
first manually-operated switch means operable to selectively drive said motor in one direction at the "slow" speed;
second manually-operated switch means operable to selectively drive said motor in the opposite direction at the "slow" speed; and
third manually-operated switch means operable in conjunction with one of said first and second switch means to drive said motor in the corresponding direction at the "rapid" speed.

4. A fluid infusion device according to claim 3 including a remote switch assembly operable by foot and connectable to said electrical system, said remote switch assembly including
fourth manually-operated switch means operable to selectively drive said motor in said one direction at the "slow" speed;
fifth manually-operated switch means operable to selectively drive said motor in said one direction at the "rapid" speed;
sixth manually-operated switch means operable to drive said motor in said opposite direction at the "slow" speed; and
seventh manually-operated switch means operable to selectively drive said motor in said opposite direction at the "rapid" speed.

5. A fluid infusion device according to claim 4 wherein said remote switch assembly includes
eighth manually-operated switch means operable to selectively open said infusion valve; and
ninth manually-operated switch means operable to selectively close said infusion valve.

6. A fluid infusion device according to claim 1 including
a second electrically-operated auxiliary fluid pump having an outlet connected in fluid communication with said first conduit means, said auxiliary pump being shut off during normal operation;
third pressure detecting means for detecting the fluid pressure in said first conduit means and producing a signal representative of a pump output pressure;
means in said electrical system for receiving said pump output pressure signal and producing an underpressure signal in response to the pump output pressure decreasing below a predetermined level; and
means in said electrical system for initiating operation of said auxiliary pump in response to said underpressure signal.

7. A fluid infusion device according to claim 6 wherein said electrical system includes
means connected to said second pressure detecting means for producing an overpressure signal in response to the pressure in said third conduit means increasing above a predetermined level;
means for causing said infusion valve to move to the closed position in response to said overpressure signal.

8. A fluid infusion device according to claim 7 wherein said electrical system includes an alarm circuit means for activating an audible alarm means in response to said overpressure signal.

9. A fluid infusion device according to claim 1 wherein said infusion valve includes a vent passage which is open to atmosphere and is connected in fluid communication with said third conduit means when said infusion valve is in the closed position.

10. A fluid infusion device according to claim 1 wherein said first and second indicating means includes temperature compensating means and are arranged so that the visual read out of said preset and infusion pressures are within 1 mm Hg of the respective actual fluid pressure in said second and third conduit means when the temperature in said housing is within the range of about 60° to about 120° F.

11. An air infusion device adaptable to provide a continuous flow of air into the vitreous cavity of a human eye during vitrectomy surgery, said device including
- a housing;
- a pressurized air outlet in said housing;
- an electrically-operated primary air pump and an electrically operated auxiliary air pump for delivering a substantially continuous flow of air, each of said pumps having an outlet and said auxiliary pump being turned off during normal operation;
- a pressure regulator disposed in said housing and having an outlet, an inlet connected in fluid comunication with the outlet of both said primary and said auxiliary pumps via first conduit means and movable adjustment means for varying the pressure of the air delivered from said regulator outlet;
- an electrically-operated infusion valve disposed in said housing and having an inlet connected in fluid communication with said regulator outlet via second conduit means and an outlet connected in fluid communication with said air outlet via third conduit means, said infusion valve being movable between an open position to permit air flow from said regulator to said air outlet and a closed position to prevent air flow from said regulator to said air outlet;
- first pressure detecting means for detecting the air pressure in said second conduit means and producing a signal representative of a preset pressure;
- second pressure detecting means for detecting the air pressure in said third conduit means and producing a signal representative of an infusion pressure substantially corresponding to the pressure of the fluid delivered through said fluid outlet;
- third pressure detecting means for detecting the air pressure in said first conduit means and producing a signal representative of a pump output pressure;
- a reversible electric motor operably connected to said regulator adjustment means for moving said adjustment means in opposite directions to increase and decrease the pressure of air delivered from said regulator outlet;
- a disposable fluid delivery unit removably connected to said air outlet and including a tube and a millipore, bacterial static filter, the inside diameter of said tube and the pore size of said filter being large enough to prevent a substantial pressure drop in the air flowing therethrough and yet the pore size of said filter being small enough to remain bacterial static; and
- an electrical control system electrically interconnecting said primary and auxiliary pumps, said motor, said infusion valve, and said pressure detecting means, said electrical system including
  - first indicating means for receiving said preset pressure signal and providing a visual read out of the preset pressure,
  - second indicating means for receiving said infusion pressure signal and providing a visual read out of the infusion pressure,
  - means for receiving said pump outlet pressure signal and producing an underpressure signal in response to the pump output pressure decreasing below a predetermined level,
  - means for initiating operation of said auxiliary pump in response to said underpressure signal, and
  - a motor control circuit for selectively driving said motor in opposite directions to increase and decrease the preset pressure and including pressure adjustment means for selectively changing the level of electrical power supplied to said motor to selectively drive said motor at a "slow" speed and at a "rapid" speed and thereby selectively change the speed at which the preset pressure is adjusted.

12. An air infusion device according to claim 12 wherein said motor control includes pressure adjustment means for selectively changing the level of electrical power supplied to said motor to selectively drive said motor at a "slow" speed and at a "rapid" speed and thereby selectively change the speed at which the preset pressure is adjusted, said pressure adjustment means including
- first manually-operated switch means operable to selectively drive said motor in one direction at the "slow" speed; and
- second manually-operated switch means operable to selectively drive said motor in an opposite direction at the "slow" speed; and
- third manually-operated switch means operable in conjunction with one of said first and second switch means to drive said motor in the corresponding direction at the "rapid" speed, and further including a remote switch assembly operable by foot and connectable to said electrical system, said remote switch assembly including
- fourth manually-operated switch means operable to selectively drive said motor in said one direction at the "slow" speed;
- fifth manually-operated switch means operable to selectively drive said motor in said one direction at the rapid speed;
- sixth manually-operated switch means operable to drive said motor in said opposite direction at the "slow" speed;
- seventh manually-operated switch means operable to selectively drive said motor in said opposite direction at the "rapid" speed;
- eighth manually-operated switch means operable to selectively open said infusion valve; and
- ninth manually-operated switch means operable to selectively close said infusion valve.

13. An air infusion device according to claim 12 wherein said electrical system includes
- means connected to said second pressure detecting means for producing an overpressure signal in response to the pressure in said third conduit means increasing above a predetermined level;
- means for causing said infusion valve to move to the closed position in response to said overpressure signal; and
- an alarm circuit means for activating an audible alarm in response to said overpressure signal.

* * * * *

UNITED STATES PATENT AND TRADEMARK OFFICE
CERTIFICATE OF CORRECTION

PATENT NO.  :  4,670,006
DATED       :  June 2, 1987
INVENTOR(S) :  Kevin B. Sinnett and Rodger L. White It is certified that error appears in the above-identified patent and that said Letters Patent is hereby corrected as shown below:

In the claims:

Column 12, line 13, "12" should read -- 11 --.

Signed and Sealed this

Twenty-second Day of September, 1987

Attest:

DONALD J. QUIGG

Attesting Officer    Commissioner of Patents and Trademarks